United States Patent [19]

Wu

[11] Patent Number: 5,149,775
[45] Date of Patent: Sep. 22, 1992

[54] METHOD FOR PURIFYING HIGH MOLECULAR WEIGHT VINYLPYRIDINE/STYRENE POLYMERS FROM SOLUTION

[75] Inventor: Stephen H. W. Wu, Kingsport, Tenn.

[73] Assignee: Eastman Kodak Company, Rochester, N.Y.

[21] Appl. No.: 647,122

[22] Filed: Jan. 25, 1991

[51] Int. Cl.$^5$ ............................ C08F 6/06; C08F 6/12
[52] U.S. Cl. ..................................... 528/493; 528/496; 528/499
[58] Field of Search ........................ 528/493, 496, 499

[56] References Cited

U.S. PATENT DOCUMENTS

| | | | |
|---|---|---|---|
| 2,830,975 | 4/1958 | Irvin | 260/82.1 |
| 3,041,243 | 6/1962 | Sugimoto et al. | 167/82 |
| 3,073,748 | 1/1963 | Utsumi | 167/82 |
| 3,275,518 | 9/1966 | Endicott et al. | 167/82 |
| 3,383,283 | 5/1968 | Brindamour | 167/83 |
| 3,619,200 | 11/1971 | Ferguson et al. | 99/2 |
| 3,623,997 | 11/1971 | Powell | 252/316 |
| 3,697,640 | 10/1972 | Grant et al. | 424/35 |
| 3,718,631 | 2/1973 | Grosmangin et al. | 260/80.72 |
| 3,829,564 | 8/1974 | Merry et al. | 424/78 |
| 3,832,252 | 8/1974 | Higuchi et al. | 156/86 |
| 3,880,990 | 4/1975 | Bauer et al. | 424/19 |
| 3,917,813 | 11/1975 | Pedersen | 424/20 |
| 3,988,480 | 10/1976 | Ames et al. | 426/2 |
| 4,181,708 | 1/1980 | Dannelly | 424/19 |
| 4,181,709 | 1/1980 | Dannelly | 424/21 |
| 4,181,710 | 1/1980 | Dannelly et al. | 424/33 |
| 4,429,113 | 1/1984 | Wu et al. | 528/486 |
| 4,443,497 | 4/1984 | Samejima et al. | 427/213 |
| 4,486,471 | 12/1984 | Samejima et al. | 427/213 |
| 4,518,769 | 5/1985 | Wu et al. | 528/486 |
| 4,533,562 | 8/1985 | Ikegami et al. | 427/3 |
| 4,563,517 | 1/1980 | Watson et al. | 528/496 |
| 4,593,082 | 6/1986 | Dombroski et al. | 526/216 |
| 4,595,584 | 6/1986 | Wu et al. | 424/19 |
| 4,717,567 | 1/1988 | Wu et al. | 424/462 |
| 4,794,166 | 12/1988 | Engelhardt et al. | 528/493 |
| 4,808,412 | 2/1989 | Smith et al. | 424/442 |
| 4,837,004 | 6/1989 | Wu et al. | 424/438 |
| 4,851,226 | 7/1989 | Julian et al. | 424/441 |
| 4,853,461 | 8/1989 | Chang et al. | 528/486 |
| 4,902,780 | 2/1990 | Bourrain et al. | 528/483 |

FOREIGN PATENT DOCUMENTS 176642 4/1986 European Pat. Off. .
888131 1/1962 United Kingdom .

OTHER PUBLICATIONS

Derwent Abstract WPI Acc. No. 68-29145Q/00 (Japanese Patent 69011915).
Derwent Abstract WPI Acc. No. 66-13441F/00 (Japanese Patent 64017167).
Derwent Abstract WPI Acc. No. 70-08627R/06 (Japanese Patent 70002031).
Derwent Abstract WPI Acc. No. 66-05490F/00 (British Patent 888,131).
Derwent Abstract WPI Acc. No. 88-252010/36 (European Patent 281,464).

Primary Examiner—Paul R. Michl
Assistant Examiner—Andrew E.C. Merriam
Attorney, Agent, or Firm—Thomas R. Savitsky; Betty J. Deaton; William P. Heath, Jr.

[57] ABSTRACT

Taste-masking composition for oral delivery of medicaments to non-ruminants, especially humans. The taste-masking composition contains a polymeric composition containing a flake material, a hydrophobic material, and a polymer containing repeating units from vinylpyridine derivatives. Also disclosed is a process for purifying polymers.

8 Claims, 12 Drawing Sheets

METHOD FOR PURIFYING HIGH MOLECULAR WEIGHT VINYLPYRIDINE/STYRENE POLYMERS FROM SOLUTION

FIELD OF INVENTION

This invention concerns a taste-masking method by use of a polymeric composition containing repeating units from vinylpyridine derivatives. Also, the invention concerns a preferred polymer purification method.

BACKGROUND OF THE INVENTION

A number of patents describe coating compositions and pellets coated therewith which are adaptable for oral administration to ruminants. The coating protects the core material of the pellets in the rumen and releases it postruminally. The coating is composed of a specific mixture of a film-forming polymeric material (I) and hydrophobic material (II), (I) and a flake material (III), or (I) and (II) and (III). Some bioactive substances, which are miscible with the basic coating polymer, can be dispersed molecularly in the polymer matrix to achieve the desirable post-ruminal delivery. U.S. patents of interest include U.S. Pat. Nos. 3,619,200; 3,880,990; 3,041,243; 3,697,640; 3,988,480; 3,383,283; 3,275,518; 3,623,997; 3,073,748; 3,829,564; 3,832,252; and 3,917,813. Of particular interest are U.S. Pat. Nos. 4,181,708; 4,181,709; 4,181,710; 4,837,004; 4,808,412; 4,717,567; and 4,595,584.

These patents only describe applications for ruminants. No non-ruminant application is disclosed.

U.S. Pat. No. 3,041,243 (1962) describes the art of sealing coat for tablets and the like. A copolymer of vinylpyridine and styrene is described in the patent. Powdered filler is added during the intermediate drying after the application of each coating so as to minimize the agglomeration during the coating process. GB Pat. No. 888,131 describes a method for preparing solid, oral medicament forms, e.g., tablets, prills and granules protecting from the action of moisture and/or oxygen by a water-insoluble, acid-soluble coating of a film-forming polymer selected from poly-2-vinylpyridine, poly-4-vinylpyridine, poly-2-methyl-5-vinylpyridine, poly-5-ethyl-2-vinylpyridine and copolymers containing at least 50% by weight of these and a comonomer such as vinyl acetate, acrylonitrile, methyl acrylate and styrene. These two patents do not describe any purification method to remove monomers and oligomers from copoly(VP/ST), nor do the patents describe functional additives which in combination with the polymer form a coating composition.

U.S. Pat. No. 4,443,497 (1984) describes a method of preparing microcapsules by conducting the phase separation of a coating polymer material in the presence of ethylcellulose. The steps include a) dissolving a coating material and ethylcellulose in a solvent, b) dispersing drug particles to the solution, c) adding to the dispersion an organic liquid which is miscible to the solvent and which is nonsolvent for said coating polymer material and the core material, thereby forming coating walls of said coating polymer material on and around the particles, and then c) recovering the thus-formed microcapsules therefrom. Ethylcellulose present in the phase separation system minimizes the coagulation of the coating polymer material. The examples of the wall forming material which can be used in the patent art include a water-insoluble, acid-soluble coating polymer material (i.e., a coating polymer material soluble in water at a pH not higher than 5).

U.S. Pat. No. 4,486,471 describes a process for making gastric release pharmaceutical microcapsules in which the wall material consists of ethylcellulose and a water-insoluble, acid-soluble polymer material. The process steps include a) dissolving ethylcellulose in a solvent, b) dispersing drug particles in the solution, c) cooling the dispersion in the presence of a water-insoluble, acid-soluble polymer material until the ethylcellulose separates out from the dispersion to form coating walls on and around the particles of said core material, and then d) recovering the thus-formed microcapsules therefrom. Active substance is rapidly released in contact with gastric juice on account of dissolution of the acid-soluble polymer material to render the microcapsule wall porous.

U.S. Pat. No. 4,533,562 describes a method of preparing coated solid preparation without the use of solvents, with a powdered film-forming polymer and with a liquid plasticizer having an affinity for the polymer. The polymers useful in the patent include polymers soluble in the stomach such as vinylpyridine/methyl acrylate methacrylate copolymer.

Japanese Pat. No. JP 70,002,031 describes a method for preparing enteric coated tablets comprising press-coating solid tablets by the use of a coating composition comprised of (i) an enteric material and (ii) an enteric material which does not swell in the gastric juice but dissolves in the gastric juice.

Another Japanese Pat. No., JP 64,017,167, describes a process for coating pharmaceutical tablets for oral administration with a water-insoluble amphoteric polymer which is soluble in acids and alkalines. The tablets or granules coated with the polymer are indefinitely stable in a moist atmosphere but rapidly disintegrate in gastric and intestinal juice with release of the medicament.

Another Japanese Pat. No., JP 69,011,915, describes a method for making capsules suitable for release of medicament in gastric juice. The medicament is coated with an acid-soluble polymer and one or two polymeric resins soluble in gastric and/or intestinal juices.

To be useful for human applications, the polymeric materials must be essentially free from or containing reasonably low residual monomers so that the polymeric materials would not cause any safety concern.

European Pat. No. 281,464 describes a purification process for removing residual monomers from styrene/vinylpyridine copolymers by selective extraction with super critical carbon dioxide gas. The process gives copolymers containing 1 ppm residual monomers.

U.S. Pat. Nos. 4,429,113 and 4,518,769 describe processes for separating high molecular weight fraction from polar polymer using polyfunctional acid or base coascervating agent to form crosslinked, coascervated polymer solids.

Another patent application no., EP 176642 A1, describes an acetic acid wash process for purifying vinylpyridine copolymers.

U.S. Pat. No. 3,718,631 describes a purification method employing extraction with pyridine in xylene.

SUMMARY OF THE INVENTION

The present invention is directed to a method for masking the taste of a medicament comprising orally administering to a non-ruminant animal a taste-masking composition comprising (1) about 0.01% to about 50% of a medicament, and (2) about 50% to about 99.99% of a polymeric composition comprising (a) a physiologically acceptable, film-forming water-miscible, acid-soluble polymeric material comprising a polymer or a mixture of polymers, the polymeric material having a molecular weight of greater than 250,000, and being resistant to digestive fluid with a pH of greater than 5.5 and soluble or swellable at a pH of less than 4.5 at the normal temperature of the stomach, said polymeric material containing at least 50% by weight of repeating units from a monomer selected from the group consisting of 2-vinylpyridine, 4-vinylpyridine, 2-methyl-5-vinylpyridine, 5-ethyl-2-vinylpyridine, and a mixture thereof;

(b) between about 0.1% and about 135%, based on the weight of polymeric material, of a hydrophobic material dispersed in the polymeric material selected from the group consisting of edible waxes, resins, polymers, fatty acids having from 12 to 32 carbon atoms, mono- and di-glycerides containing acyl chains having 12 to 32 carbon atoms, and polyfunctional carboxylic acids having a ratio of from 10 to 22 carbon atoms per carboxyl group; and (c) greater than about 100% and up to about 567% based on the weight of said polymeric material, of a physiologically acceptable flake material dispersed in the polymeric material.

The present invention is also directed to a preferred polymer purification process. More specifically, the present invention is also directed to a process for purifying high molecular weight polymers comprising (A) dispersing with agitation a 2-vinylpyridine/styrene or 4-vinylpyridine/styrene polymer fraction containing residual monomers, low molecular weight polymers of a number average molecular weight less than 10,000 and high molecular weight polymers of a number average molecular weight greater than 100,000 in a solvent system comprising (i) acetone, methyl ethyl ketone, or a mixture thereof, and (ii) about 0.1% to about 12%, based on the total weight of the solvent system, of water, methanol, ethanol, or a mixture thereof, under conditions such that a major portion of the high molecular weight polymers are swollen and a major portion of the residual monomers and low molecular weight polymers are soluble in the solvent system, and (B) allowing the dispersion of step (A) to settle to form a gel-like layer with a supernatant followed by decanting the supernatant.

As used herein, the numbers immediately following the description of a particular polymer refer to the respective weight contributions of each monomer to the final polymer composition. For example, "4-vinylpyridine/styrene (80/20)" or "poly(4-vinylpyridine-co-styrene, 80/20)" refers to a polymer containing 80% repeating units from 4-vinylpyridine and 20 weight % repeating units from styrene.

DETAILED DESCRIPTION OF THE INVENTION

Figure 1:
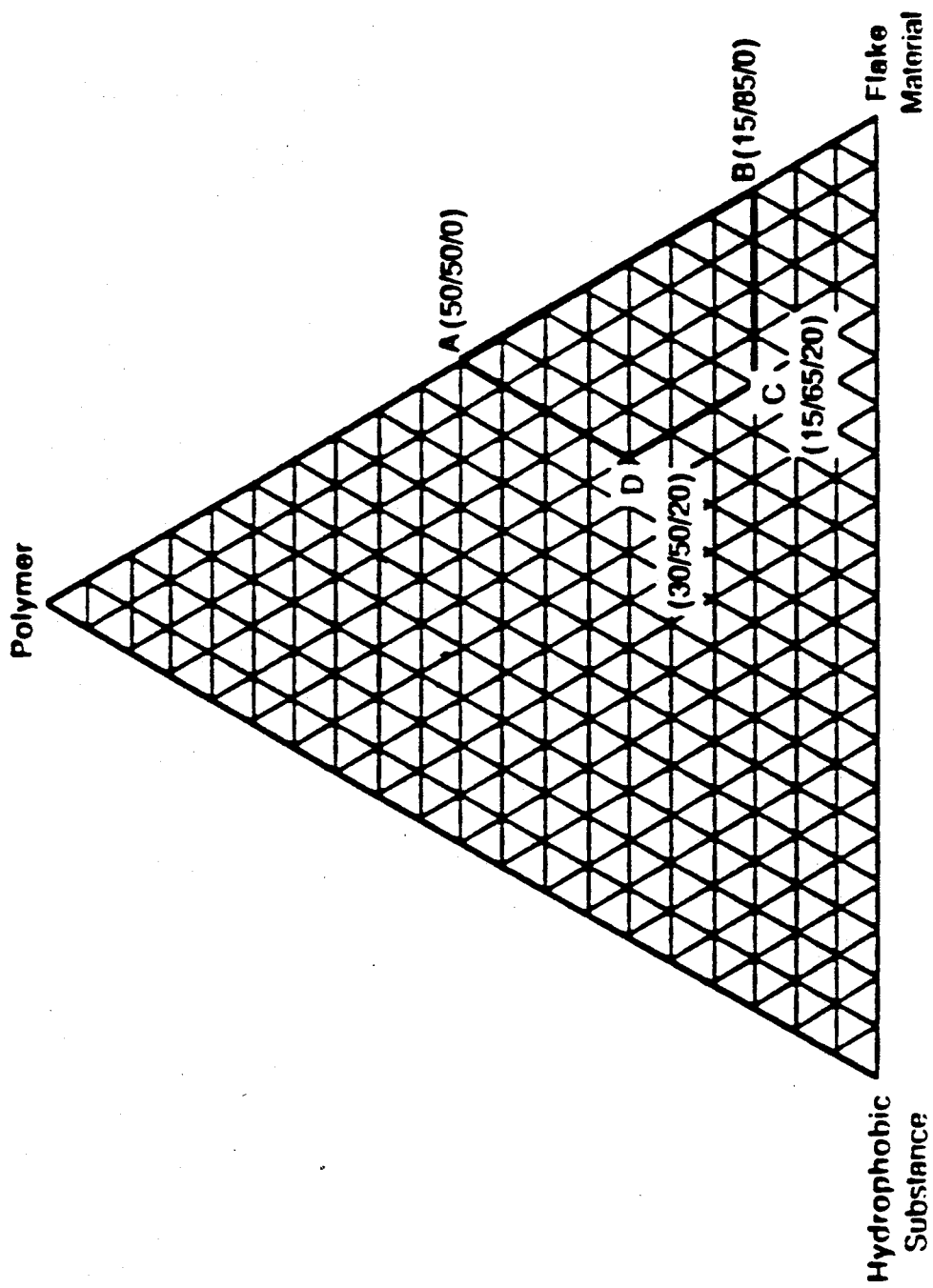
FIG. 1—Tri-component graph of the preferred weight percentages of the component of the polymeric composition as defined by lines AB, BC, CD, and DA.

The polymeric composition of the taste-masking composition comprising a), b) and c) is physiologically acceptable and resistant to a pH of greater than about 5.5, but capable of releasing the coated active ingredients at a pH of less than 4.5. Thus substrates coated with the coating compositions will remain intact in contact with saliva, but rapidly disintegrate in the stomach.

The taste-masking composition can be applied to a pharmaceutical core material in the form of particulates, pills, beads, or tablets by first dissolving/dispersing the coating materials in a suitable solvent system and then spraying the coating dope onto the core material via common pharmaceutical coating processes such as using pan coater, or fluid bed coater. The coating material is capable of forming a continuous film around the cores by evaporation of solvent from the coating material.

The coated core has the ability to protect active drugs in the core from immediately releasing to saliva in the mouth and the ability to expose the core material in the stomach juice and release the active drugs in the core rapidly or in a slow release fashion thereafter.

In addition, said taste-masking composition can be in the form of a medicament molecularly dispersed in a matrix of said polymeric composition, wherein said medicament is miscible with the polymeric material and has a solubility of less than 5 g/100 g of water at 25° C. Such molecularly dispersed compositions and preparation thereof are described in U.S. Pat. No. 4,808,412, incorporated herein by reference in its entirety.

It is preferred that the polymeric material contains 0.1 to 50% by weight of repeating units derived from monomers selected from the group consisting of vinyl acetate; acrylonitrile; a $C_1$-$C_4$ alkyl acrylate such as methyl acrylate, methyl methacrylate, ethyl methacrylate, and the like; styrene; and a mixture thereof.

The medicament of the taste-masking composition of the invention is one which is bitter, sour or otherwise objectionable to the end user. Such medicaments include, but are not limited to: antibiotics, antihistamines, decongestants, antitussives, expectorants, and a mixture thereof. Specific examples include efrotomycin, erythromycin, methionine, potassium chloride, chlorpheniramine, dextromethorphan, phenylephrine, guaifenesin, and a mixture thereof.

It is also possible to use the taste-masking composition of the invention to mask the taste of poisons such as warfarin, sodium cyanide, sodium trifluoroacetate, and the like to assist in exterminating undesirable pests such as rats, mice, opossums, and the like. Humans are specifically and preferably contemplated as a non-ruminant animal within the scope of the method of the invention.

It is optional that the taste-masking composition further comprises about 0.1 to about 95%, preferably about 20% to about 90%, based on the total weight of the taste-masking composition, of at least one other additive. Such additives include, but are not limited to, plasticizers such as triacetin, diethyl phthalate, dibutyl phthalate, acetyl tributyl citrate, triethyl citrate, dibutyl sebacate, polyethylene glycol, polysorbate 80, and a mixture thereof.

In the taste-masking composition, it is preferred that component (1) is present in an amount of about 10 to about 40 weight %, and component (2) is present in an amount of about 60 to about 90 weight %. Also preferred is wherein said polymeric composition comprises about 1.5% to about 121% of component (b) and about 200% to about 485% of component (c), said percentages being based on the weight of component (a). More preferred is wherein said polymeric composition comprises about 5% to about 80% of component (b) and about 206% to about 380% of component (c), said percentages being based on the weight of component (a).

Regarding the hydrophobic material and flake material of the polymeric material of the invention, many different types can be employed and examples of such materials can be found in U.S. Pat. No. 4,837,004, incorporated herein by reference in its entirety. It is preferred wherein said hydrophobic material is selected from the group consisting of waxes, resins, polymers, fatty acids having from 12 to 32 carbon atoms, aluminum salts of fatty acids having from 12 to 32 carbon atoms, and polyfunctional carboxylic acids having a ratio of from 10 to 22 carbon atoms per carboxyl group, and said flake material is selected from the group consisting of talc, aluminum flake, graphite, ground mica and combinations thereof.

In the polymer purification process of the invention, it is preferred that step (B) is followed by the additional step of (C) repeating steps (A) and (B) for a total of 2 to 6 cycles.

In the polymer purification process it is also preferred wherein said solvent system further comprises 0.001% to about 4% acetic acid and/or that the temperature of the dispersion is raised to about the boiling temperature of component (i) (e.g., about 56° C. if component (i) is acetone). If the dispersion is heated, it is preferable to cool to less than about 40° C., more preferably about room temperature, before separation of the supernatant from the gel-like layer. The preferred means of separation of the supernatant from the gel-like layer is by decantation. A small amount of succinic acid optionally can be added to enhance polymer gel formation.

Even more preferred is wherein step (C) of the polymer purification process is followed by the additional steps of (D) adding an amount of water to the dispersion of step (A) effective to form a clear solution; and (E) removing the acetone or methyl ethyl ketone by evaporation, or adding an additional amount of water to the dispersion so as to result in a precipitation of a major portion of the high molecular weight polymer from the dispersion.

In the polymer purification process, also preferred is wherein the total amount of water added to the dispersion is greater than about 40% based on the total weight of the dispersion.

Of course, it is preferred that the polymeric material used in the taste-making method of the invention is prepared by the polymer purification process of the invention.

The invention is further illustrated by the following non-limiting examples.

EXAMPLES

Abbreviations optionally used herein have the following meaning: 2VP=2-vinylpyridine, ST=styrene, 4VP=4-vinylpyridine, 2M5VP=2-methyl-5-vinylpyridine, DMF=dimethylformamide, b.p.=boiling point, MW=molecular weight, v or vol.=volume, W or wt.=weight, ppb=parts per billion, $MW_n$ or Mn=number average molecular weight, I.V.=inherent viscosity, m=meter, mL=milliliter, lb.=pound.

EXAMPLE 1 pH Dependent Solubility of Polymers

Figure 2:
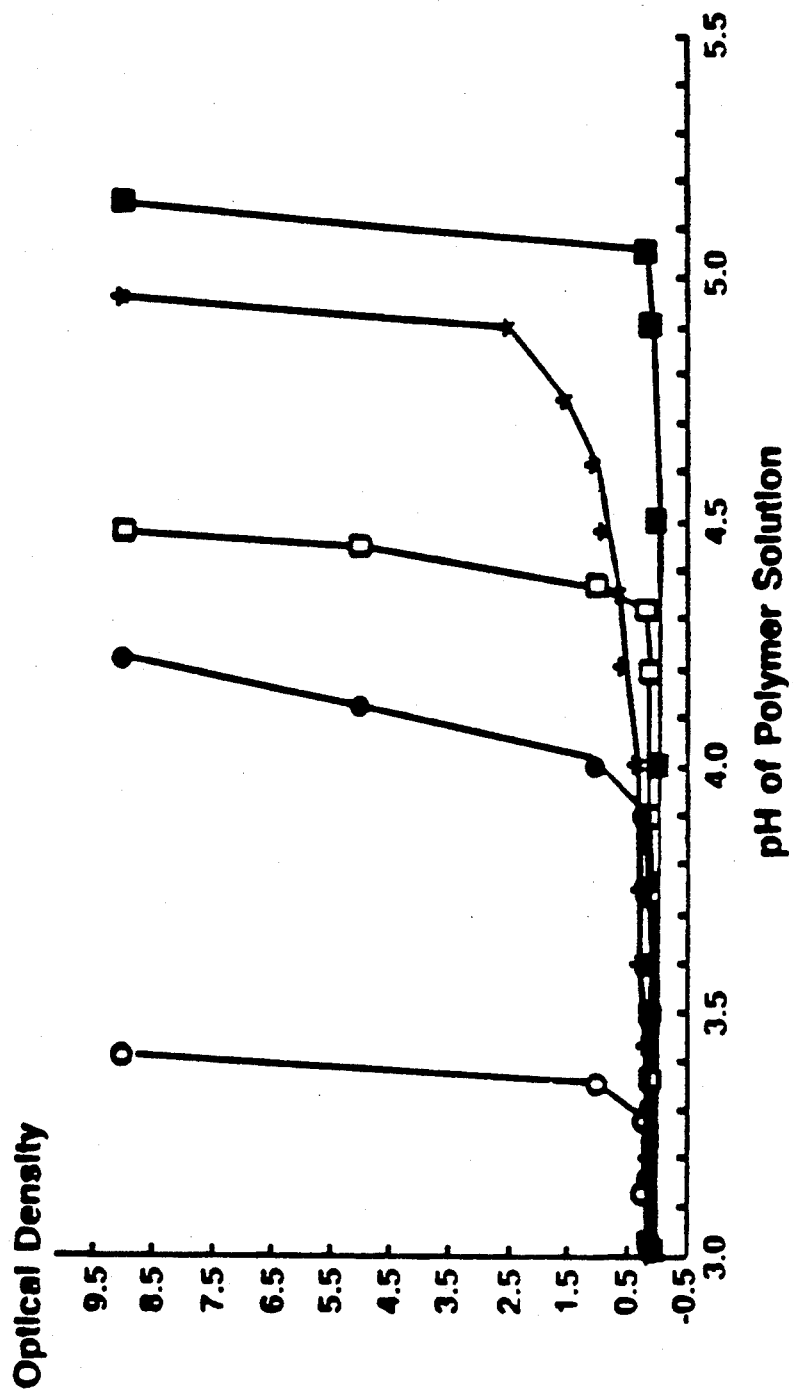
FIG. 2—Turbidity titration of vinyl-pyridine copolymers. The symbols "o" represent 4-vinylpyridine/styrene (80/20), the symbols "•" represent 2-methyl-5-vinylpyridine/styrene (80/20), the symbols "□" represent 2-vinylpyridine/styrene (80/20), the symbols "*" represent 2-methyl-5-vinylpyridine/methylmethacrylate (80/20), and the symbols "■" represent 2-methyl-5-vinylpyridine (100).

This example illustrates pH-dependent solubilities of polymers containing vinylpyridine moieties. All polymers used in this example are soluble in pH 1.2 simulated gastric fluid containing sodium chloride and hydrochloric acid. These polymers are also soluble in a pH 2.9 buffer containing citric acid and dibasic sodium phosphate. A 0.1% polymer solution (wt. by vol., pH 2.9) is then titrated with 0.2 N NaOH solution to determine the cloud point pH at which polymer becomes insoluble (FIG. 2). The results are as follows:

| Polymer | Cloud Point pH |
| --- | --- |
| poly(2-methyl-5-vinylpyridine) | 5.0 |
| poly(2-methyl-5-vinylpyridine-co-methyl-methacrylate, 80/20) | 4.8 |
| poly(2-vinylpyridine-co-styrene, 80/20) | 4.4 |
| poly(2-methyl-5-vinylpyridine-co-styrene, 80/20) | 4.0 |
| poly(4-vinylpyridine-co-styrene, 80/20) | 3.4 |

Considering the characteristic pH's of a human digestive system, pH of saliva in the mouth is neutral at about 7.0, pH of the stomach juice ranges approximately from pH 1.2 at fast state to a value less than 5.0 at a fed state. In the following examples, pH 2.9 and 5.5 buffers are used as extracting media to show the effectiveness of coating compositions described in the respective examples.

EXAMPLE 2

Solubilities of Selected Polymers in Acetone/Methanol

This example illustrates solubility of poly(2VP/ST, 80/20) and poly(4VP/ST, 80/20) in acetone/methanol. It also illustrates that solubility of these two polymers in acetone/methanol depends on polymer concentration and the ratio of acetone/methanol in the solvent system. These two polymers are soluble in methanol, but insoluble in acetone. However, these two polymers are swellable in acetone. Thus, when these two polymers are dispersed in acetone, two distinct layers are formed; the polymers swell and form a gel-like layer in the bottom of the container with the top layer being a liquid.

It is important to note that poly(2-methyl-5-vinylpyridine-co-styrene, 80/20) is soluble in acetone; no gel layer is found in the acetone solution (no swelling occurs). Thus the formation of gel layers for poly(2-or 4-VP/ST, 80/20) or other polymers alike in acetone is unexpected.

Figure 3:
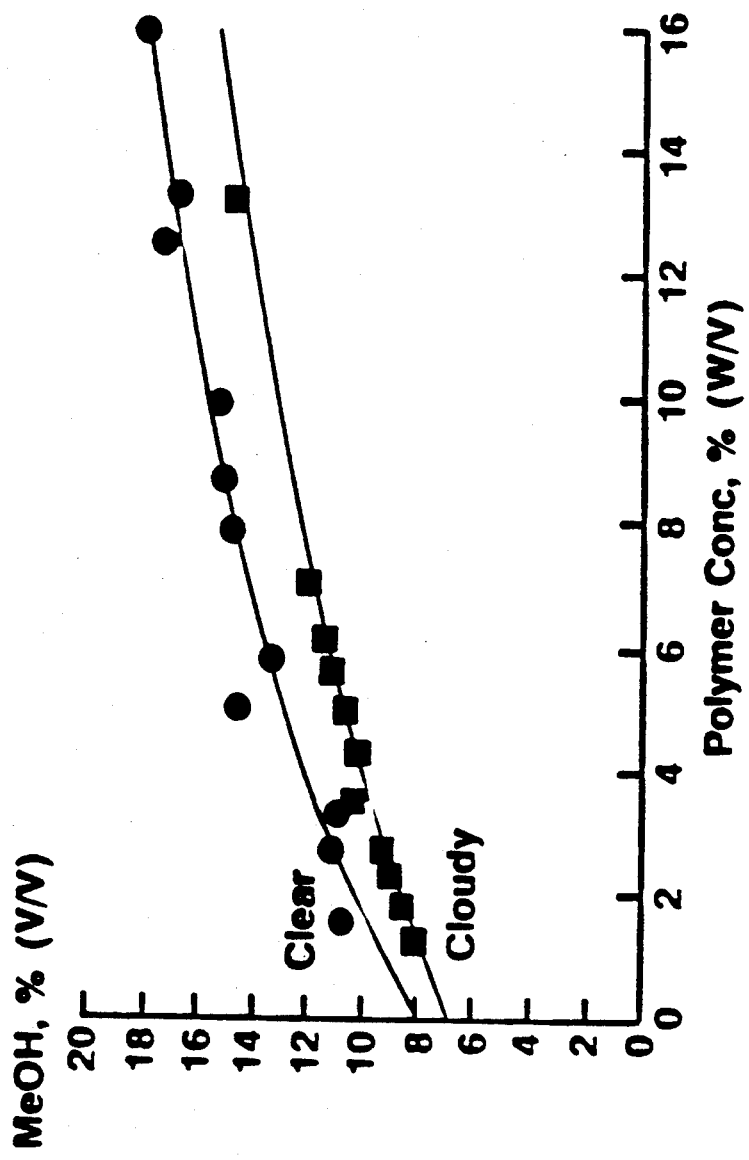
FIG. 3—Solubility of 2-vinylpyridine/styrene (80/20) and 4-vinylpyridine/styrene (80/20) in a solution of acetone and various amounts of methanol. The symbols "•" represent 2-vinylpyridine/styrene (80/20) having an inherent viscosity (I.V.) of 0.7 in dimethylformamide (DMF), the symbols "■" represent 4-vinylpyridine/styrene having an I.V. of 1.08 in DMF. "V/V" is volume/volume and "W/V" is weight/volume.

A small amount of methanol is gradually added to the polymer/acetone system to determine the minimum amount of methanol required for dissolving the polymers in the solvent system. The relationship is shown in FIG. 3. These results indicate that adjusting the ratio of acetone/methanol and polymer concentration in the solvent system changes the polymer state from gel-like to completely soluble. This is a basis for purifying polymers from residual oligomers and monomers since oligomers and monomers exhibit higher solubility in acetone or acetone/methanol in which the polymer does not dissolve, but in which it swells and forms a gel structure.

EXAMPLE 3

Solubilities of Selected Polymers in Acetone/Water

Figure 4:
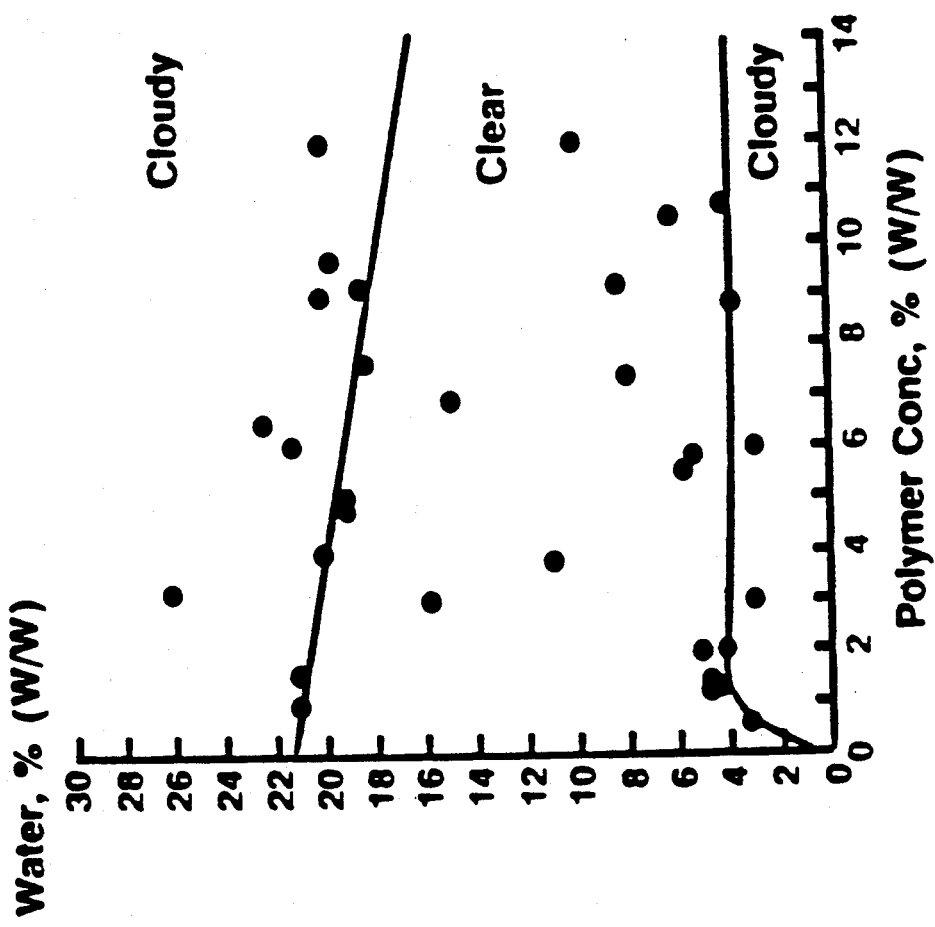
FIG. 4—Solubility of 2-vinylpyridine/styrene (80/20) in a solution of acetone and various amounts of water. "W/W" is weight/weight.
Figure 5:
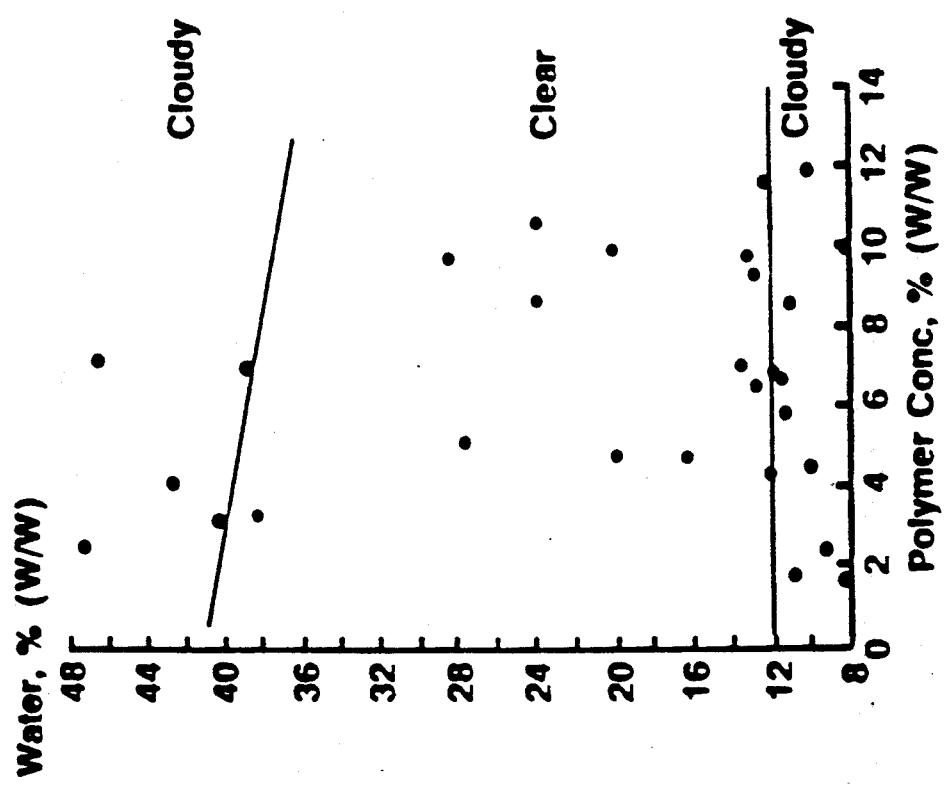
FIG. 5—Solubility of 4-vinylpyridine/styrene (80/20) in a solution of acetone and various amounts of water. "W/W" is weight/weight.

This example illustrates the solubility characteristics of poly(2VP/ST, 80/20) and poly(4VP/ST, 80/20) in acetone/water systems. The minimum amount of water in acetone/water system required for completely dissolving poly(2VP/ST, 80/20) is approximately 4% (W/W). Between 4 to about 18% poly(2VP/ST, 80/20) is completely soluble in acetone/water, but the polymer forms a gel-like layer at less than 4%, or starts to precipitate at about 18% of water in an acetone/water system. Similarly, poly(4VP/ST, 80/20) dissolves in acetone/water when the amount of water is between 12 to about 36% depending on polymer concentration in acetone/water system (FIGS. 4 and 5). The polymer forms a gel-like layer at less than about 12% water or starts to precipitate at about 36% water in an acetone/water system. The solubility characteristics of these polymers in acetone/water can be used to purify polymers from residual oligomers and monomers in the polymers.

EXAMPLE 4

A Method for Purifying Selected Polymers

This example illustrates a purification method based on the solubility difference of monomers, oligomers and polymers in acetone and binary solvent systems such as acetone/water, acetone/ethanol, and acetone/methanol. 2-Vinylpyridine and styrene monomers and oligomers (MW<2000) are soluble in acetone, methanol, ethanol, and in acetone with a trace amount of water, methanol, and ethanol. High molecular weight poly(2VP/ST, 80/20) is soluble in methanol and ethanol, but insoluble in acetone. It was found that the copolymer becomes swollen as a gel in acetone and the gel phase becomes loose and less viscous when a trace amount of water, methanol, or ethanol is introduced into the solvent system. When the ratio of acetone/water or acetone/methanol reaches a certain critical limit as shown in the previous examples (Examples 2 and 3) the polymer becomes soluble. These observations suggest that poly(2VP/ST) can be purified by either fractional precipitation or a fractional solution method.

In the fractional precipitation method, successive precipitation of polymer species is achieved by addition of a miscible nonsolvent and the larger molecules precipitate first. In the fractional solution method, polymer is directly and successively extracted with a liquid of increasing solvent power so that monomers are extracted, then oligomers, and larger molecules remain in the gel or swollen solid phase. The fractional solution method is found to be particularly suitable because of the high yield of the product and the simplicity for developing a scaleup process. The following procedures are used to purify copoly(2VP/ST, 80/20) samples which have inherent viscosity values from 0.66 to 1.45.

Procedure 1—Extraction with Acetone

1. Disperse 25 grams of poly(2VP/ST, 80/20) in pure acetone.
2. Raise the temperature of the dispersion to the boiling temperature of acetone (56° C.). (This step is optional.)
3. Cool the dispersion and allow the polymer layer to settle, and decant the supernatant.
4. Repeat Steps 1-3 three to five times.

Procedure 2—Extraction with Acetone/Water

This procedure is similar to Procedure 1 except that the solvent system contains a small portion of water (acetone/water, 98/2, or 99/1 v/v) and the heating/cooling steps may be carried out at the boiling temperature of the solvent system or simply repeating extraction at room temperature.

Procedure 3—Extraction with Acetone/Ethanol, or Acetone Methanol

This procedure is similar to Procedure 1 except that the solvent system is acetone/ethanol in which ethanol is less than 10% by vol, or acetone/methanol in which methanol is less than 4% by vol. The heating and cooling steps may be carried out at the b.p. of the solvent system or simply repeating extraction at room temperature.

A small amount of acetic acid may be added in the solvent system but not sufficient enough to dissolve the polymer gel. If it is desired to increase the yield of polymer in the purification process, succinic acid may be added to enhance polymer gel formation.

Figure 6:
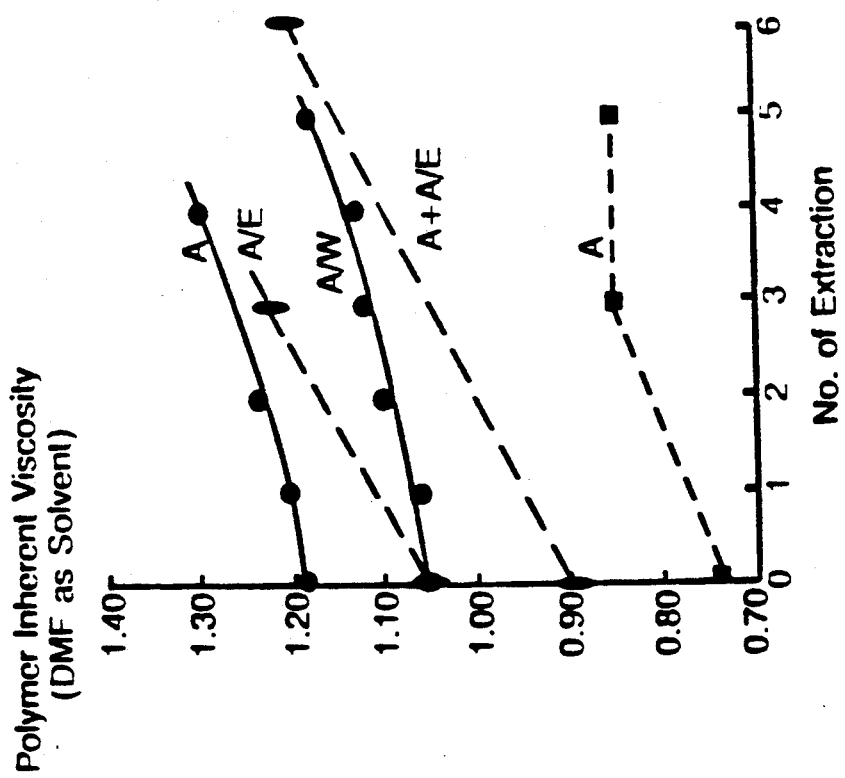
FIG. 6—Inherent viscosities (I.V.'s) of 2-vinylpyridine/styrene (80/20) after extraction with various solvents. The units for inherent viscosity herein are deciliters/gram. The "•" symbols associated with the upper solid line labelled A represent extraction with acetone, the "♦" symbols associated with the upper broken line labelled A/E represent extraction with a solution containing 95 volume % acetone and 5 volume % ethanol, the "•" symbols associated with the lower solid line labelled A/W represent extraction with a solution containing 98.5 volume % acetone and 1.5 volume % water, the "♦" symbols associated with the middle broken line labelled A+A/E represent extraction with acetone (3 extractions) followed by extraction with a solution containing 90 volume % acetone and 10 volume % ethanol (3 extractions), and the "■" symbols associated with the lower broken line labelled A represent extraction with acetone.

Table 1 shows the results of using these procedures to purify the polymer. These results indicate the following:

1. High MW (Mn>100,000) copoly(2VP/ST, 80/20) can be purified by simply extracting the polymer with acetone (Procedure 1). The monomer contents, both styrene and 2-vinylpyridine, of the purified polymer after four to five extractions are less than 200 ppb.
2. The oligomer contents in the polymer progressively decrease as the number of extraction increases. It appears that three extractions with acetone, acetone/methanol, or acetone/ethanol are sufficient to reduce the oligomer content below 50ppm.
3. The inherent viscosities of the subsequent purified polymers increase by approximately 0.1–0.3 unit from the value of initially unpurified polymers (FIG. 6). The extent of the I.V. increase depends on the initial I.V., the solvent system used and the number of extractions. The increase in average I.V. indicates the removal of oligomers (MWn<2000) and the low molecular weight species from the starting polymer sample.
4. The yield of purifying a polymer sample by Procedures 1-3 is approximately 85-90%. However, the yield can be improved to >90% if succinic acid is used.

EXAMPLE 5

Relationship of Molecular Weight and Inherent Viscosity for Poly(2-vinylpyridine-co-styrene, 80/20)

This example illustrates the linear relationship of number average molecular weight and inherent viscosity value of poly(2VP/ST, 80/20) using DMF as a solvent in the measurement. The inherent viscosities (I.V.) are determined according to ASTM D2857-70 procedure in a Wagner Viscometer of Lab Glass Inc., of Vineland, New Jersey, having an 0.4 m capillary and a 1 mL bulb, using a polymer concentration of 0.25% by weight in dimethylformamide solvent. The procedure comprises dissolving the sample at 25° C. and measuring the flow of time at 25° C. The I.V. is then calculated from the equation:

$$(\eta)^{25° C.}_{.25\%} = \frac{\ln \frac{t_s}{t_o}}{C}$$

wherein:
$(\eta)$ = inherent viscosity at 25° C. at a polymer concentration of 0.25 g/100 mL of solvent;
ln = natural logarithm;
$t_s$ = sample flow time;
$t_o$ = solvent-blank flow time; and
C = concentration of polymer in grams per 100 mL of solvent.

Molecular weight is measured as styrene equivalent using a gel permeation chromatography method.

Figure 7:
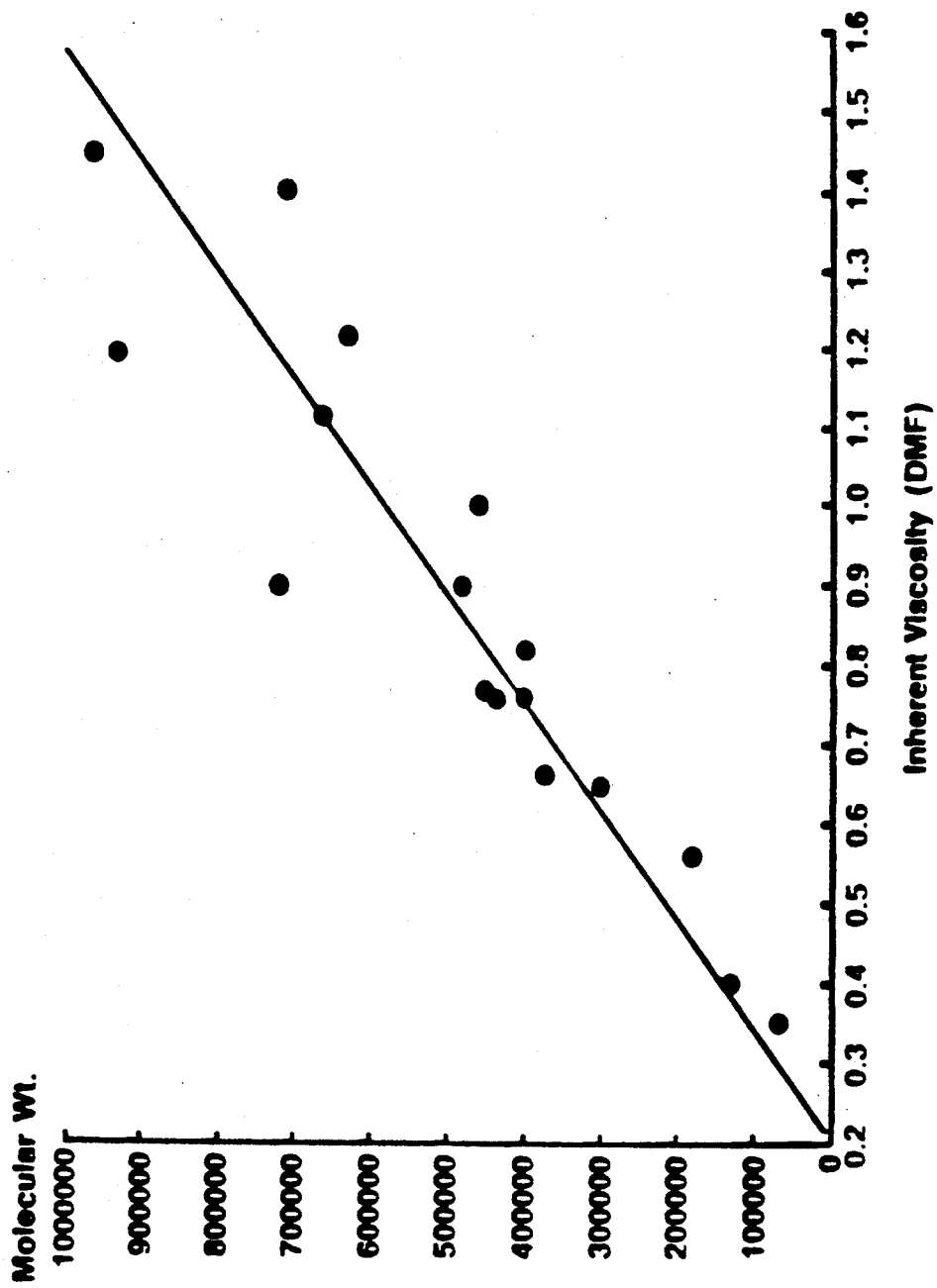
FIG. 7—Relationship of molecular weight and inherent viscosity for 2-vinylpyridine/styrene (80/20).

The relationship is given in FIG. 7.

EXAMPLE 6

Solvent Compositions for Applying the Coating Compositions

Figure 8:
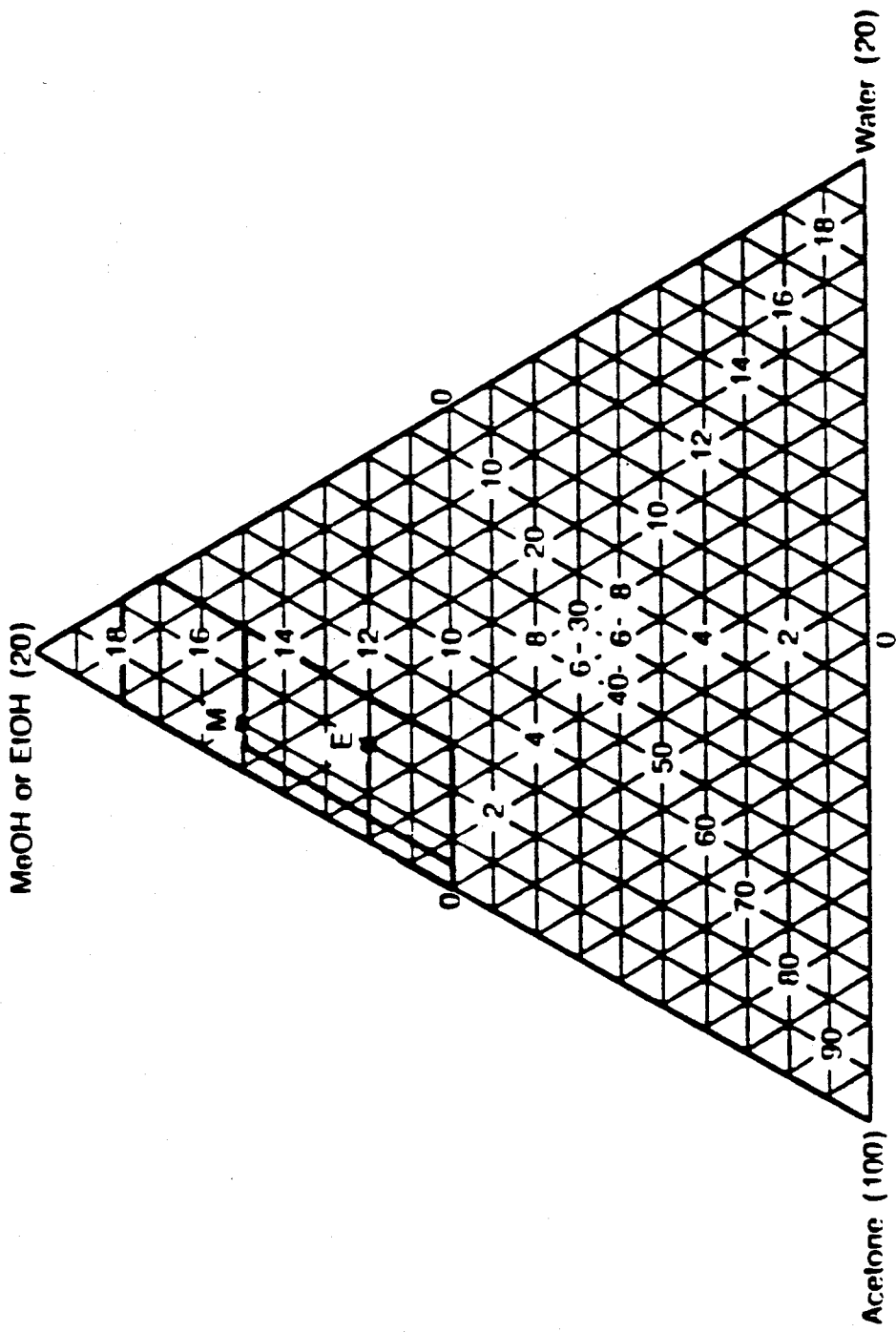
FIG. 8—Tri-component graph of solvent systems for 2-vinylpyridine/styrene (80/20). The point M is 84 volume % acetone, 15 volume % methanol, and 1 volume % water. The point E is 86 volume % acetone, 12 volume % ethanol, and 2 volume % water.

This example illustrates the solvent compositions suitable for dissolving the polymer and serving as a vehicle for carrying other coating components in a typical pharmaceutical coating process using a pan coater or an air-suspension coater. Though common solvents such as methanol and ethanol can be used as a vehicle, the relatively high polarity and boiling points prevent these two solvents from readily evaporating from the coalescing film sprayed onto the substrates. Thus the surfaces are usually tacky and agglomeration is usually observed. The solvent composition described as follows eliminates these disadvantages. Furthermore, the purified polymer in acetone as a gel-like material as obtained from Example 3 can be converted to solution readily by adjusting the solvent compositions as described in this example since acetone is the major component in the solvent system. The solvent system composition is shown in FIG. 8.

EXAMPLE 7

Pellets Coated with Polymer Only

This example illustrates that a pellet containing highly water-soluble materials coated with poly(2-methyl-5-vinylpyridine-co-styrene, 75/25) does not exhibit desirable protection and release of the active ingredient in the core. The polymer used in this example has an inherent viscosity (using DMF as solvent) of 0.51. Glucose and microcrystalline cellulose (90/10 by wt.) are granulated to form rounded pellets by a process consisting of wet mixing, extrusion, pelletization, and rounding steps. Wet pellets are then dried and sieved to −12/+16 mesh (U.S. Standard). Glucose pellets are then coated with the polymer in a solvent system as described in Example 4 to a coating level of 15% using an air-suspension coater. One gram of the coated pellets is extracted in 50 mL of pH 5.5 buffer for 24 hours as a test for protection. Approximately 65% of glucose remains in the core, and 35% is released into the aqueous medium. Another one gram of the coated pellets is extracted in 50 mL of pH 2.9 buffer. Approximately 70% of glucose remains in the core. These results show that polymer alone as a coating does not provide quick release in an acidic medium nor provide adequate protection for the active ingredient, glucose.

EXAMPLE 8

Pellets Coated with Polymer and Hydrophobic Substance

Glucose pellets as prepared in Example 6 are coated with a coating composition consisting of 85% poly(2M5VP/ST, 80/20) which has an I.V. of 0.51 and 15% stearic acid. One gram of coated pellets is extracted in pH 5.5 buffer for 24 hours. 95% Glucose remains in the pellets. However, when another one gram of coated pellets is extracted in pH 2.9 buffer for 1 hour, only about 30% glucose is released from the pellets.

Another sample of glucose pellets is coated with a coating composition consisting of 65% polymer and 35% stearic acid. Very significant electrostatic build-up is observed during the coating process, and pellets are agglomerated in the coater. However, the protection value for glucose at pH 5.5 is 90%, and the release is nearly complete when coated pellets are extracted in pH 2.9 buffer for 1 hour.

EXAMPLE 9

Pellets Coated with Polymer, Stearic Acid and Aluminum Flake

Glucose pellets are coated with a coating composition consisting of 60% poly(2M5VP/ST, 80/20) which has an inherent viscosity of 0.51 using DMF as a solvent, 26% stearic acid and 14% aluminum flake. The coated pellets exhibit a good protection of 89% after 24 hours extraction in pH 5.5 buffer, and complete release after 1 hour at pH 2.9.

The addition of aluminum flake in the coating composition reduces the electrostatic problem slightly. The coatability of the coating composition is judged to be poor. Substantial agglomeration of pellets in the coater is observed. Another sample of glucose pellets is coated with a coating composition consisting of 56% polymer, 11% stearic acid and 33% bentonite or aluminum flake. The coatability is significantly improved.

The protection value of glucose is better than 90% after 24 hours extraction in pH 5.5 buffer, and the release of glucose is complete when coated pellets are extracted in pH 2.9 buffer for 1 hour.

This example indicates the use of functional flake materials in the coating composition provides good performance and process ease to apply the coating composition.

EXAMPLE 10

Pellets Coated with a Blend of Polymers and Other Coating Components

Glucose pellets are coated with a coating composition consisting of 38% poly(2M5VP/ST, 80/20) which is a 50/50 mixture of the polymers with different inherent viscosity values, 0.5 and 2.1, 6% stearic acid and 56% talc. The glucose protection value is 85% at pH 5.5 after 24 hours, and the pellets completely disintegrate in pH 2.9 buffer in 1 hour. No agglomeration is observed in the coating process.

EXAMPLE 11

Pellets Coated with Polymer, Talc and Stearic Acid

Glucose pellets are coated with a composition consisting of 30% poly(2M5VP/ST, 80/20) with an I.V. value of 1.0 or 1.57, 3% stearic acid and 67% talc. When both pellets are extracted in pH 5.5 buffer for 24 hours, the protection values exceed 95% and the coated pellets completely disintegrate in pH 2.9 in 1 hour. No electrostatic problem and pellet agglomeration is observed in the coating process.

EXAMPLE 12

This example illustrates that it is important for the polymer to have an I.V. value greater than 0.5 to be effective in the coating composition; the preferred I.V. is 0.8–1.2. The relationship of I.V. and MW is shown in Example 4.

Figure 9:
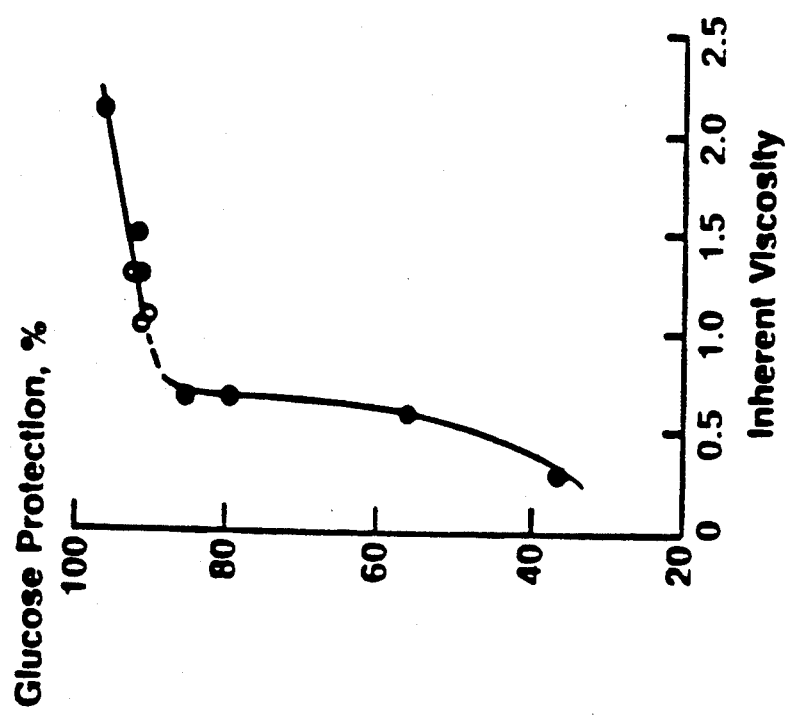
FIG. 9—Effect of inherent viscosities of 2-methyl-5-vinylpyridine/styrene (80/20) in the coating formulation on glucose protection at pH 5.5. The weight ratio of polymer:pigment:stearic acid in the coating formulations was 31.5:65:3.5. The symbols "•" represent a coating composition containing a weight ratio of talc:aluminum flake of 40:60. The symbols "o" represent a coating composition containing a weight ratio of talc:aluminum flake of 60:40.

Glucose pellets are coated with a coating composition comprising poly(2M5VP/ST, 80/20), a combination of talc and aluminum flake, and stearic acid. The ratio is 31.5/65/5.0 by weight. The polymer I.V. ranges from 0.3 to 2.0. Pellets are extracted in pH 5.5 buffer for 24 hours. The protection values are plotted as a function of I.V. of the polymer. The results are shown in FIG. 9.

The example indicates that it is important for the polymer to have a high I.V. value (at least about 0.5, preferably about 0.5 to about 2.5, more preferably about 0.8 to about 1.5) to be useful for the disclosed coating composition.

EXAMPLE 13

Figure 10:
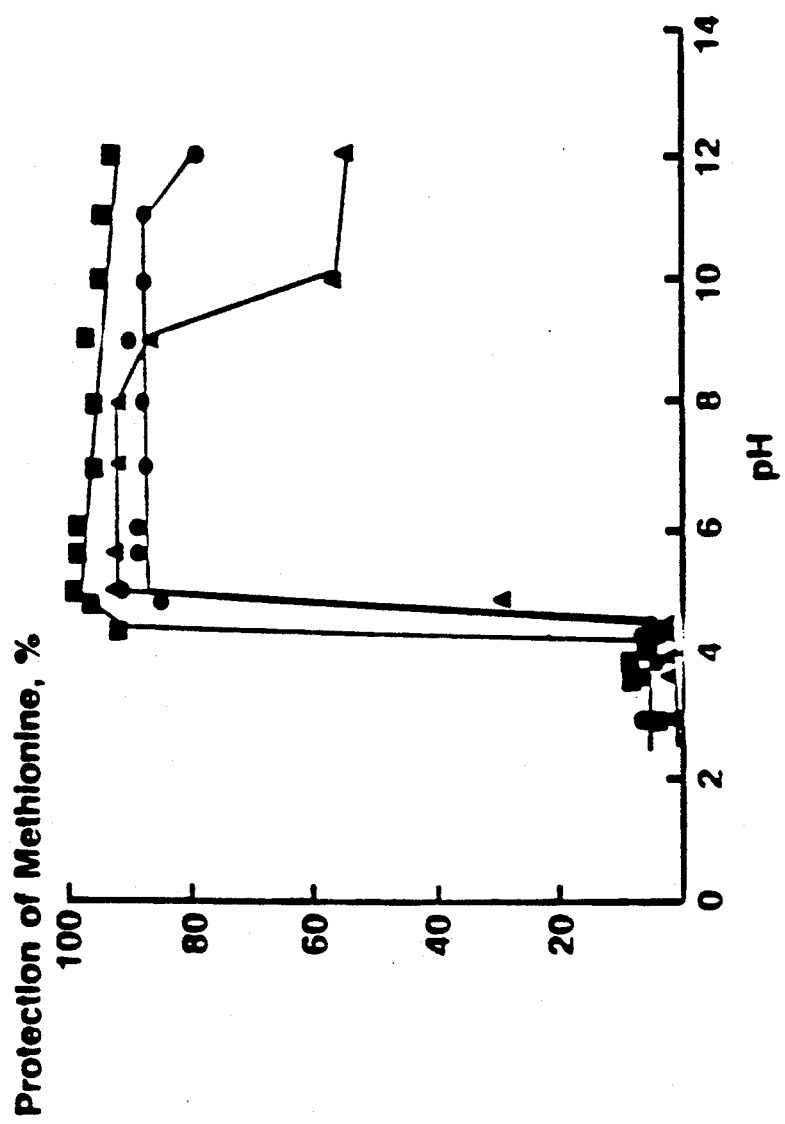
FIG. 10—The pH profile of the protection of methionine cores coated with coating compositions of the invention. The coating compositions contained a weight ratio of polymer:talc:stearic acid of 31.5:63.5:5. The symbols "■" represent a composition wherein the polymer was 2-vinylpyridine/styrene (80/20), the symbols "•" represent a composition wherein the polymer was 2-methyl-5-vinylpyridine/styrene (80/20), and the symbols "▲" represent a composition wherein the polymer was 4-vinylpyridine/styrene (80/20).

This example illustrates that a bitter taste, low water solubility active ingredient such as methionine can be protected at pH 4.5 or above with a coating composition comprising a polymer having an I.V. of 1.0 such as poly(2VP/ST, 80/20), poly(2M5VP/ST, 80/20), poly(4VP/ST, 80/20), talc, and stearic acid at a ratio of 31.5/63.5/5.0 by weight. Methionine pellets coated with the said composition are extracted in buffer solutions with a pH value range from 2.5 to 12 for 24 hours. The results are shown in FIG. 10.

EXAMPLE 14

This example illustrates the quick release characteristics of the coating.

Figure 11:
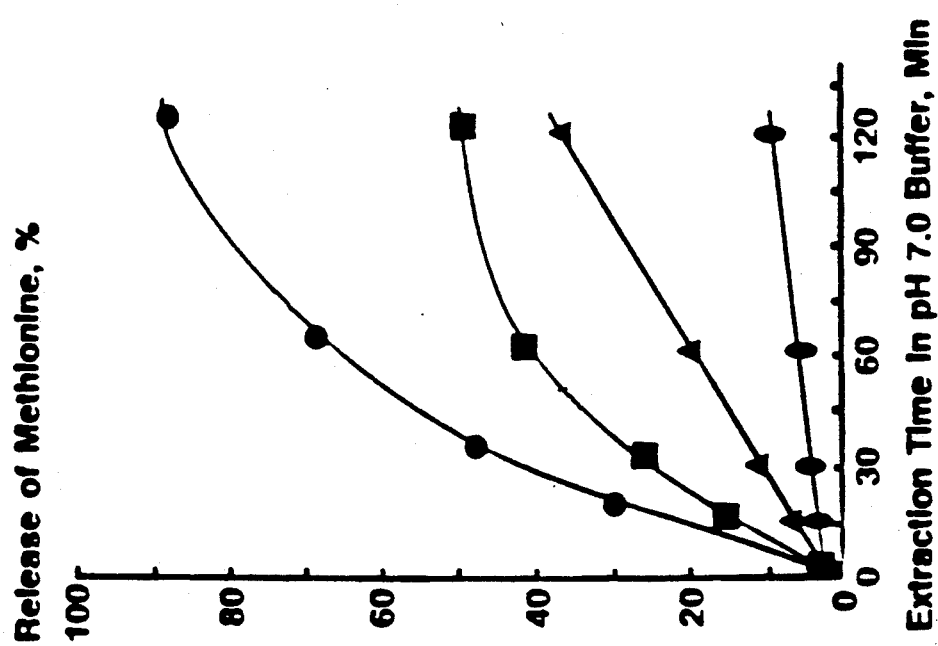
FIG. 11—Release characteristics of methionine from methionine cores coated with coating compositions of the invention after short contact with pH 2.9 buffer followed by pH 7.0 buffer for various times. The coating compositions contained a weight ratio of polymer:talc:stearic acid of 31.5:63.5:5. The polymer was 2-methyl-5-vinylpyridine/styrene (80/20). The symbols "◆" represent contact with pH 7.0 buffer for 0.5 minute, the symbols "▲" represent contact with pH 7.0 buffer for 1 minute, the symbols "■" represent contact with pH 7.0 buffer for 2 minutes, and the symbols "●" represent contact with pH 7.0 buffer for 5 minutes.

Methionine pellets coated with the coating composition as given in Example 12 are extracted with pH 2.9 buffer for a very short period of time, 0.5, 1.0, 2.0, and 5.0 minutes respectively. The buffer solution is then adjusted to a pH value of 7.0. Though methionine is not very water soluble, the results indicate that the coating is irreversibly damaged to allow methionine continuously released from the pellets (FIG. 11).

EXAMPLE 15

Polymer/Active Ingredient in a Matrix System

This example illustrates that an antibiotic drug can be molecularly dispersed in the polymeric matrix and that the polymer/drug complex can be applied to an inert carrier to form a dosage form.

A coating dope is prepared by dissolving 29.6 grams of poly(2VP/ST, 80/20) and 5.9 grams of efrotomycin, an antibiotic drug, in 500 mL of acetone/methanol/water (85/15) and adding 4.7 grams of stearic acid to the polymer solution until it is completely dissolved and then dispersing 59.7 grams of talc into the solution while maintaining stirring. In an air-suspension coater, 170 grams of glucose pellets or granules (particle size, $-20/+60$ mesh) are coated with the said coating dip to a coating level of 15% by weight. The coated pellets are extracted in pH 7.0 and 5.5 buffer solutions. The coating remains intact. However, when pellets are extracted in pH 1.2 or 2.9 buffer solutions, the coating rapidly dissolves to allow drug dispersed into the extracting medium in about 30 minutes.

EXAMPLE 16

Figure 12:
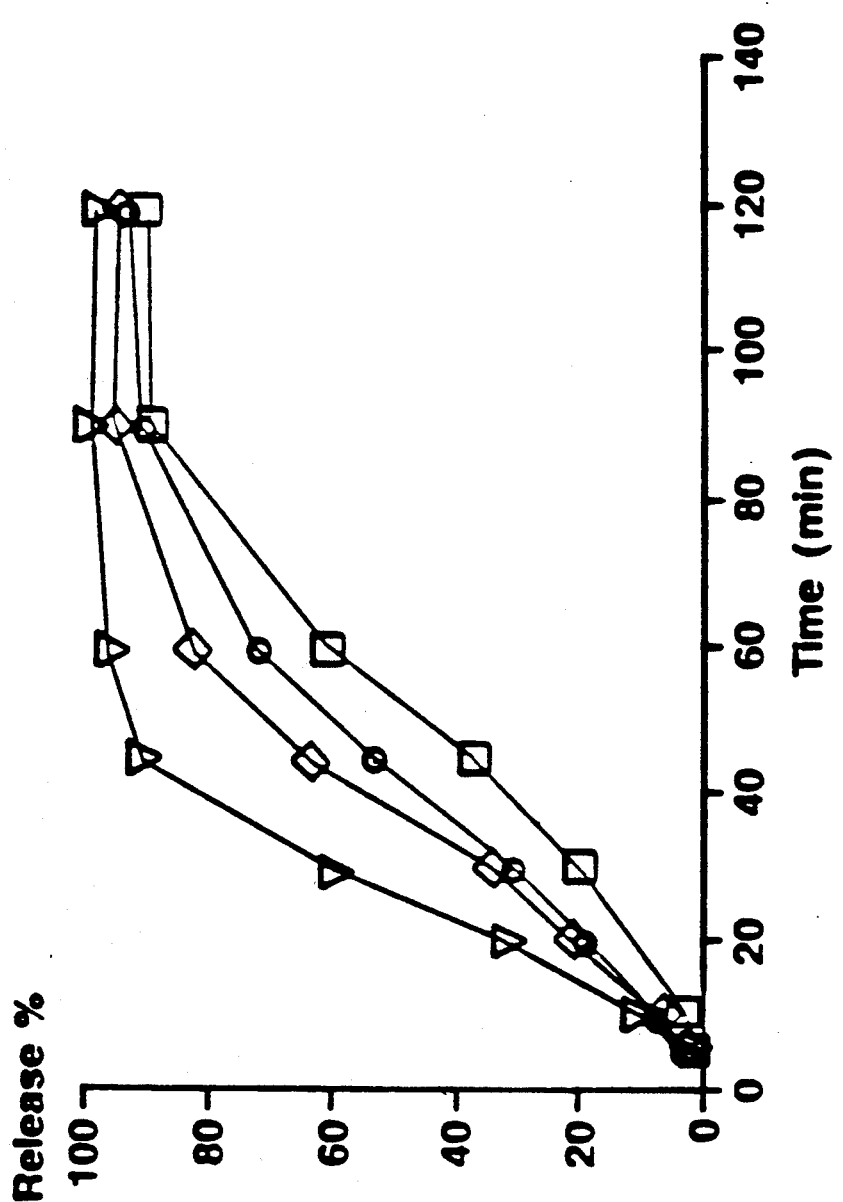
FIG. 12—Effect of miscible additives on efrotomycin release from a matrix of efrotomycin and the coating composition of the invention. The matrix was prepared as described in Example 15 hereof. The symbols " " represent a composition containing a weight ratio of polymer:efrotomycin of 80:20, the symbols "∇" represent a composition containing a weight ratio of polymer:efrotomycin:ascorbic acid of 70:20:10, the symbols "○" represent a composition containing a weight ratio of polymer:efrotomycin:triacetin of 70:20:10, and the symbols "□" represent a composition containing a weight ratio of polymer:efrotomycin:oleic acid of 70:20:10.

Selected compatible additives and plasticizers can be added to the polymer/drug matrix to alter the release rate or to modify the mechanical properties of the coating. Typical examples are ascorbic acid, triacetin, stearic acid, and oleic acid. FIG. 12 shows the effect of these additives on release of efrotomycin from a polymer/drug matrix.

can be effected within the spirit and scope of the invention.

I claim:

1. A process for purifying high molecular weight polymers comprising
   (A) dispersing with agitation a 2-vinylpyridine/styrene or 4-vinylpyridine/styrene polymer fraction containing residual monomers, low molecular weight polymers of a number average molecular weight less than 10,000 and high molecular weight polymers of a number average molecular weight greater than 100,000 in a solvent system comprising
      (i) acetone, methyl ethyl ketone, or a mixture thereof, and
      (ii) about 0.1% to about 12%, based on the total weight of the solvent system, of water, methanol, ethanol, or a mixture thereof.
   under conditions such that a major portion of the high molecular weight polymers are swollen but a major portion of the residual monomers and low molecular weight polymers are soluble in the solvent system, and
   (B) allowing the dispersion of step (A) to settle to form a gel-like layer with a supernatant followed by separating the supernatant from the gel-like layer.

2. The process of claim 1 wherein the separation of the supernatant from the gel-like layer is accomplished by decantation.

3. The process of claim 2 comprising the additional step of
   (C) repeating steps (A) and (B) for a total of 2 to 6 cycles.

TABLE 1

Results of Purifying Copoly(2VP/ST, 80/20)

| Purification Procedure | Solvent System (v/v) | Extraction (Times) | I.V. (in DMF) | Oligomers[1] (MW <2000) ppm | Monomers[2] (ppb) 2VP | ST |
|---|---|---|---|---|---|---|
| I | Acetone | 0 | 0.66 | 681.3 | >200 | 367 |
|   |         | 5 | —    | 46.0  | —    | —   |
|   | Acetone | 0 | 1.10 | >200  | >200 | >200 |
|   |         | 5 | 1.34 | <5.0  | 37   | 70[3] |
|   | Acetone | 0 | 1.19 | >200  | —    | —   |
|   |         | 4 | 1.30 | 6.0   | <200 | <200 |
| II | Acetone/H₂O (98.5/1.5) | 0 | 1.05 | 233.7 | | |
|   |         | 1 | 1.06 | 152   | | |
|   |         | 2 | 1.10 | 40    | | |
|   |         | 3 | 1.12 | 33.2  | | |
|   |         | 4 | 1.13 | 16.4  | | |
|   |         | 5 | 1.18 | 15.8  | | |
| III | Acetone/Ethanol (75/25) | 0 | 1.05 | 233.7 | | |
|   |         | 3 | 1.23 | 8.94  | | |
| I & III | Acetone and Acetone/Ethanol (90/10) | 0 | 0.895 | 614.9 | | |
|   |         | 3(A) + 3(A/E)[4] | 1.20 | 50.7 | | |
|   |         | 3(A) + 3(A/E) | 1.20 | 16.7 | | |
| I | Acetone | 0 | 1.45 | 20.6 | | |
| I & III | Acetone and Acetone/Ethanol (90/10) | 3(A) + 3(A/E) | 1.64 | 17.9 | | |
| III | Acetone/Ethanol (90/10) | 3(A/E) | 1.61 | 4.1 | | |
| I & III | Acetone and A/E (86.5/13.5) | 0 | 1.18 | 85.1 | | |
|   |         | 3(A) + 3(A/E) | 1.36 | 10.4 | | |

[1] Determined by a UV spectrometric method.
[2] Determined by a GC-mass spectrometric method.
[3] 50 lb. batch purified in a pilot plant.
[4] A = acetone and A/E = acetone/ethanol. Thus, 3(A) + 3(A/E) indicates three extractions with acetone followed by three extractions with a mixture of acetone and ethanol in the indicated v/v amounts.

The invention has been described in detail with particular reference to preferred embodiments thereof, but it will be understood that variations and modifications 4. The process of claim 1 wherein said solvent system further comprises 0.001% to about 4% acetic acid.

5. The process of claim 4 wherein said solvent system further comprises succinic acid.

6. The process of claim 2 wherein the dispersion is raised to about the boiling temperature of component (i) and then cooled to less than about 40° C. prior to separation of the supernatant from the gel-like layer.

7. The process of claim 3 comprising the additional steps of (D) adding an amount of water to the dispersion of step (A) effective to form a clear solution; and (E) removing the acetone or methyl ethyl ketone by evaporation, or adding an additional amount of water to the dispersion so as to result in a precipitation of a major portion of the high molecular weight polymer from the dispersion.

8. The process of claim 7 wherein the total amount of water added to the dispersion is greater than about 40% based on the total weight of the dispersion.

* * * * *